United States Patent [19]

Proctor, Jr.

[11] Patent Number: 4,782,701
[45] Date of Patent: Nov. 8, 1988

[54] TRANSDUCER FOR MEASURING TRANSIENT TANGENTIAL MOTION

[76] Inventor: Thomas M. Proctor, Jr., 22901 Old Hundred Rd., Barnesville, Md. 20838

[21] Appl. No.: 31,870

[22] Filed: Mar. 30, 1987

[51] Int. Cl.⁴ .............................................. G01N 29/00
[52] U.S. Cl. ...................................... 73/587; 310/327; 310/334; 310/336
[58] Field of Search .................. 73/587, 658; 310/327, 310/334, 367, 369, 336

[56] References Cited

U.S. PATENT DOCUMENTS

| | | | |
|---|---|---|---|
| 3,553,501 | 1/1971 | Thill | 310/327 |
| 3,580,057 | 5/1971 | Seegmiller | 310/336 |
| 4,088,907 | 5/1978 | Jones et al. | 73/587 |
| 4,461,177 | 7/1984 | Feng | 73/587 |
| 4,701,658 | 10/1987 | Ringermacher et al. | 310/327 |

OTHER PUBLICATIONS

M. W. Godfrey, L. A. Mahmood, & D. C. Emmony, "An Improved Design of Point Contact Transducer", *NDT International*, vol. 19, Apr. 1986, pp. 91–93.

F. R. Breckenridge, "Acoustic Emission Transducer Calibration by Means of the Seismic Surface Pulse", *J. Acoustic Emission*, vol. 1, 1982, pp. 87–94.

ASTM, "Standard Method for Primary Calibration of Acoustic Emission Sensors", 1986 ASTM Standards, Section 3, vol. 03.03, pp. 949–969.

*Primary Examiner*—John Chapman

[57] ABSTRACT

A transducer is provided for measuring tangential dynamic displacement of a transient nature at a point location on the surface of a mechanical body. This broadband transducer is particularly useful for detection and measurement of acoustic emission signals. The essential components are a large, extended compound backing (1), a sensing piezoelectric element of low geometric symmetry (2) having the proper static polarization, an electrode system (3) and (4), an attachment process (3a), and a means of leveling the transducer (5). The element is characterized by two parallel plane faces of contact, the area of the rear face of attachment being much larger than the front face. The front face has a width dimension which is small in comparison to the wavelength of the highest frequency of interest.

2 Claims, 2 Drawing Sheets

TRANSDUCER FOR MEASURING TRANSIENT TANGENTIAL MOTION

STATEMENT AS TO RIGHTS TO INVENTION MADE UNDER FEDERAL SPONSORED RESEARCH AND DEVELOPMENT

The invention described herein may be manufactured and/or used by or for the U.S. Government for governmental purposes without the payment of any royalty thereon.

BACKGROUND OF INVENTION (1) Technical Field

This invention is concerned with improving the capability and extending the useful features of electromechanical acoustic emission detectors, for detecting acoustic emission signals that are emitted by solid objects with those signals being caused, for example, by material cracking and converting the signals obtained into electrical signals that replicate closely the actual dynamic displacements producing said detection. The transducer described herein responds to a very specific displacement, that is a displacement associated with tangential motion only. The object of this invention is to provide a broadband detector for dynamic tangential surface motion. Another object of this invention is to provide a broadband detector that acts as a point receiver for dynamic tangential surface motion. Its sensitivity has the inverse distance relationship expected of a point receiver. Another object of this invention is to provide a broadband measuring transducer that acts as a point receiver for dynamic tangential surface displacement which can be calibrated to measure absolute tangential surface displacement.

(2) Background Art

Acoustic emission, to which the present invention particularly applies, is concerned with the detection of elastic waves that are emitted from some source located within a solid object and becomes manifest at surfaces remote from the source. Several sources can be emitting at the same time. Often acoustic emission signals occur as a result of crack growth when external stresses are applied to the object that contain the crack. Examples of such stress induced acoustic emission signals can be found in pressure vessels under pressure test or in operation, in welded joints that support some force load while in service, as well as fatigue cracking that may be generated in a structure by a dynamically varying load. Chemical changes or temperature differences associated with this object may also induce acoustic emission.

Traditional acoustic emission transducers in use similar to those described in U.S. Pat. Nos. 3,855,847 and 4,011,472 do not produce voltage outputs that are related to some specified physical quantity, such as dynamic displacement. They are usually resonant in character, having sensitivities that change radically over the nominal frequency range of interest.

Besides questionable frequency response and response to unknown physical quantities, traditional acoustic emission transducers may respond to an unknown sum of different directional components of the surface motion. For instance, these transducers may have sensitivity to both normal and tangential motion, a situation that further confuses the interpretation of the transducer's voltage output. (Normal or tangential motion is motion that is in a direction that is respectively perpendicular to or parallel to the surface at the point of interest.) Another problem that most traditional acoustic emission transducers suffer from is related to the extended contact face. This contact face represents an aperture through which the stress wave energy must pass and as such gives rise to an interference problem for vibrational signals impinging on the front face of the transducer from off-axis positions. This adversely affects both the frequency bandwidth and the spacial sensitivity in a way that is both complicated difficult to assess. Thus traditional acoustic emission transducers are detectors of mechanical motion only and can not be used to obtain quantitative measurement of actual physical displacement or velocity.

Instead of being confined to doing triangulation or inerring the general size of the acoustic emission event from signals that are highly confused by transducer resonances and questionable mode of operation, there is a trend now towards trying to measure the actual valve of a specific physical quantity, for example, displacement or velocity of the surface. A few new transducers have been designed to produce voltage outputs that are faithful reproductions of the normal displacement of the surface over a very wide frequency range. But these transducers measure the normal component of the displacement, while the subject transducer measures the tangential component only.

Because acoustic emission signals come from any position in the soild object of interest, signals arriving at the receiving transducer come by various kinds of wave energy or modes of vibrations. There is a mode that travels along the surface which is known by the names Rayleigh or Lamb. There is a vibrational mode that comes by body waves in which the local displacement is parallel to the path of travel of the wave; this is known as the compressional mode. There is a vibrational mode that comes by body waves in which the local displacements are at right angles to the path of travel of the wave; this is known as the shear mode. The wave energy of each mode travels with a different and unique speed; a distinguishing feature. In the general case, at the location of the receiving transducer, the surface would experience the effects of all the impinging modes of vibration. The complex time-vibrational motion that occurs at one point on the surface contains information about the geometry of the body, about the size and kind of an acoustic emission event, and about the acoustic characteristics of the body media.

If the transducer were a perfec device it would sense the surface motion in its complex form ie. a sum of all the different modes of vibration and from all the different paths leading from the acoustic emission event to the receiving transducer position. This includes single and multi reflection paths as well as combinations of body waves where mode conversion is present. It also includes elastic energy that travels along a path that is contained in the surface. If the performance of the transducer is dominated by the unknown response characteristics alluded to in the previous paragraphs, the output becomes so complicated and clouded with the unknown character of the transducer that any interpretation of direct physical quantities such as surface displacement becomes virtually impossible. The ideal acoustic emission detection needs to faithfully measure one known physical quantity, such as displacement, over a wide frequency range that includes the frequencies of interest and it should be known to be sensitive to motion along one component only of the principal directions of the surface such as normal or tangential directions. The directional and spatial sensitivity should vary in a known and well controlled manner. To date no transducer design exists that can provide a faithful voltage representation of the tangential motion of a point on the surface of a solid. It is to this application that the present invention is directed.

SUMMARY

The disclosed broadband transducer is capable of detecting small dynamic tangential displacements of a transient nature at a point location on the surface of an elastic mechanical body. The high quality response of this transducer is achieved by the sensing element design that suppresses cross dimensional resonances and achieves a small acoustic aperture for the frequency band of interest and by a extended compound backing design that transmits stress wave energy out of the element and that also absorbs and scatters said stress wave energy in the backing. Because of the clean (free of spurious resonances) flat response and freedom from aperture interference effects, the disclosed transducer can be calibrated making it particularly useful for measuring absolute displacements of a dynamic tangential kind.

DESCRIPTION OF THE PREFERRED EMBODIMENT

Figure 1A:
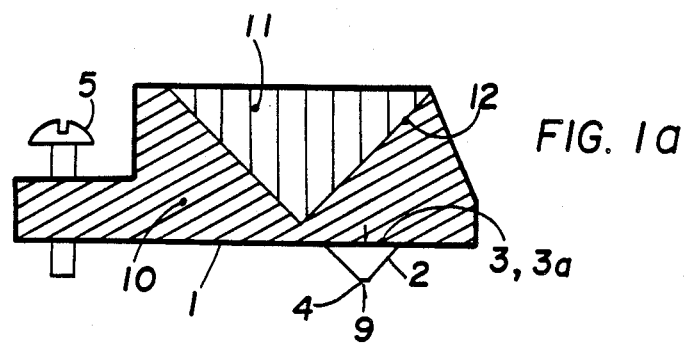
FIG. 1a is a side view and FIG. 1b bottom view of the acoustic emission transducer for tangential motion.
Figure 1B:
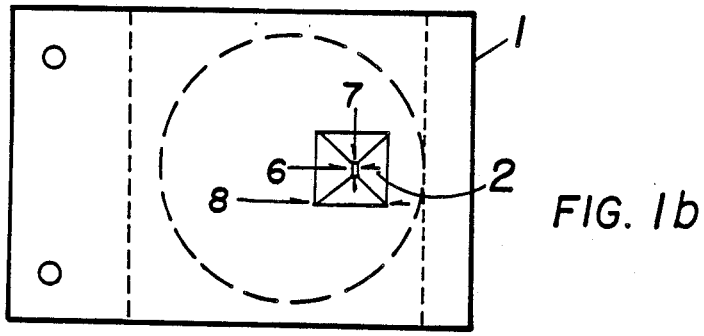
Figure 2:
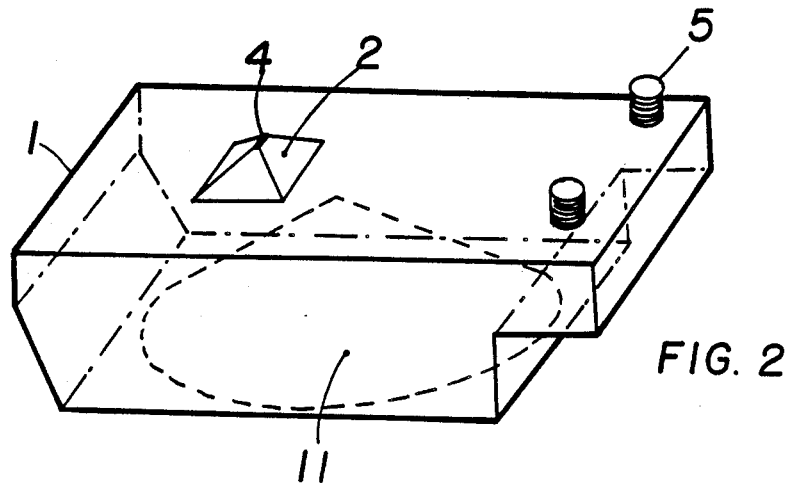
FIG. 2 is a perspective view of the transducer.

FIG. 1a and 1b show the tangential motion sensing transducer in two views, a side sectional, and a bottom view. FIG. 2 shows a perspective view of the transducer lying on its back. The present invention consists of four main components, but may also have two or three additional minor parts. The essential components are a large, extended compound backing (1), a sensing element of low geometric symmetry (2), an electrode system (3) and (4), an attachment process (3a), and a means of leveling the transducer (5). The sensing element (2) is fabricated from some piezoelectric material selected to have similar acoustic properties to the body generating the acoustic emission. Materials suitable for use as the piezoelectric sensing element are composite piezoelectric ceramic polycrystalline materials such as barium titanate, lead zirconate, lead metaniobate, lead zirconate titanate (PZT) and mixtures thereof with each other that can be statically polarized in one direction to produce the necessary ferroelectric state. The fabricated piezoelectric sensing element (2) must be polarized in a direction which is parallel to the plane of the sensing electrodes (3) & (4). Some natural piezoelectric crystals of a single crystal nature, having the proper cut can also be used. Quartz AT,BT, or YT type are examples. The active element (2) of the disclosed device is PZT but is not necessarily limited to that material. The active element (2) must be made to or have the ability to respond only to motion which is parallel to the sensing electrodes (3) & (4). This is accomplished by the proper electrode positions and by insuring that the polarized field is exactly parallel to the sensing electrodes (4), (3). The shape of the element may take different forms which produce geometries of special lower symmetry. One characteristic that describes this said lower symmetry is that the ratio of the area of the base electrode (3) to the area of the tip electrode (4) of the active element should be a large number. The tested device has a ratio that is greater than 200. One such example of a satisfactory geometry is pyramidal in shape as is shown here; another is conical. Both the areas of the base (3) and the tip electrodes (4) are flat and parallel to each other and have very thin metal layers that are attached. Nickel electrodes of less than 0.02 mm thickness are used in the device described here for electrical contact, (3) and (4). Other metals may be used for electrode purposes. Tip contact area (4) should be small in dimension compared to the desired upper frequency cut off of the device. For this device which was designed for an upper frequency limit of 2 MHz, the tip dimensions are 0.5 mm (6) and 1.0 mm (7). The active element (2) has a square base of 12 mm on a side (8) and a height of 6 mm (9). Certain other irregular geometric shapes and sizes of transducer elements might be used with equally good results. An important feature of the geometry of transducer element (2) is that it not have a constant cross section such as that of a disk or a cylinder. This consideration helps suppress cross dimensional resonances associated with a unique constant cross component dimension.

Because of fabrication errors it is difficult but still possible to produce active elements that have a zero component of the static polarization normal to the plane of the electrodes. Such a normal component of polarization would make them show some normal sensitivity, an undesirable feature. To avoid this, before assembly, fabricated transducer elements (2) should be tested by measuring the charge output from the measuring electrodes, (3) and (4), while applying a static force that is perpendicular to the plane of the electrodes. During this test, the measured charge should be zero. Any electrical charge measured during such a test indicates the presence of some normal sensitivity and will be detrimental to the purity of the response to the tangential mode of motion.

The backing (1) is compound and is made of two segments, each serving different acoustic functions. The general characteristics of the compound backing (1) are that the backing (1) be asymetrically positioned with regard to the location of the center line of the active element (2), that the backing (1) should have dimensions that are significantly larger than the active element (2), and that the backing (1) should have a shape that causes mechanical vibrations emanating out of the active element (2) to be reflected many times within the backing (1) before these vibrations chance to intersect and reenter the active element (2) again. The first segment of the backing (10) shall be constructed of a material with acoustic properties quite similar to that of the active element. In this case the first segment of the backing (10) is made of brass, which is a close acoustic match for the active element (2) which is PZT; but it is not necessarily limited to this material. The second segment of the backing (11) consists of a cavity filled with a material that has high absorption and scattering of ultrasonic energy in the frequency range of operation of the transducer. This filled cavity (11) should have an extensive interface (12) in contact with the first element of the backing (10). This filled cavity (11) should have a volume that is comparable to the volume of the first element of the backing (10). It should have a similar acoustic impedance to that of the first element (10). In this case the filled space (11) is filled with pure tin. The tin of (11) completely wets the brass of (10) so the interface is free of voids that could cause reflections. Other highly attenuative materials might be used as a filler for the cavity of (11).

The attachment process (3a) that adheres the active element (2) to the backing (1) at the position of the base electrode (3) should be acoustically very transparent to the stress waves that originate in the active element (2). Very little stress wave energy should be reflected back into the element at this interface of the base electrode (3). Besides matching acoustical characteristics, the attachment process (3a) should bond the backing (1) to the active element (2) producing a strong mechanical coupling. This attachment process (3a) should also provide electrical contact between the backing (1) and the active element (2). This consideration has been fulfilled by making the matching surface of the active element and the backing flat and smooth and by using a low temperature metal solder to produce the thin joint. In this case a tin-indium solder has been used to adhere the active element (2) to the brass backing (10).

A means of leveling the transducer assembly so that the tip area of the active element (4) can be made to sit flat on the surface of the test body is a necessity. In the version shown here, a three point mount is arranged using the tip of the active element (4) as one leg and two adjustable insulating screws (5) as the other two. Other means that allow the tip area to sit flat to the surface of the test body could be used.

Other additional but minor parts might be an electrical insulating case to provide electrical isolation from stray electrical fields. Such a case would have to be electrically isolated from the backing but at the same time it should provide physical support and protection for the basic transducer. It should also be built so that it does not electrically load down the voltage output of the transducer. This can be done by providing a driven voltage shield. Another minor part might be the inclusion of a very thin protective metal covering for the protruding tip of the active element. Such a protective cover is discussed in the literature by Godfrey, Mahmood, and Emmony.

Figure 3:
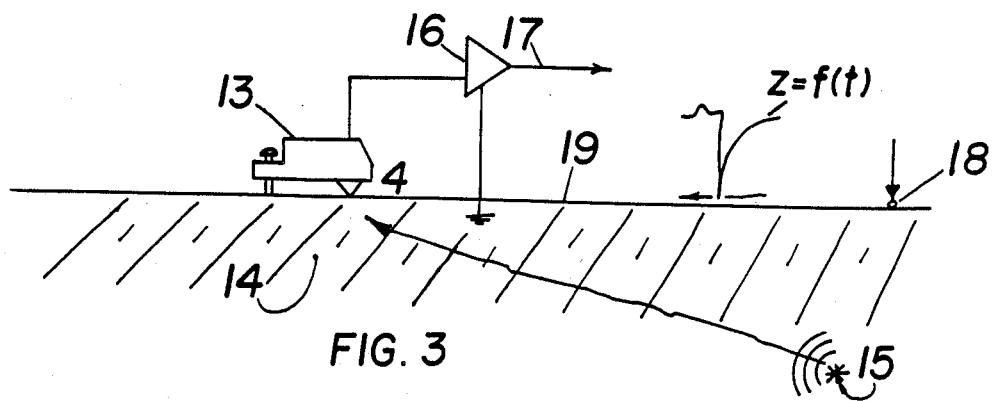
FIG. 3 is a schematic of the transducer mounted on the test surface and showing the measurement hookup.

FIG. 3 shows the arrangement of the transducer (13) sitting on the surface of the object (14) which is emitting mechanical vibration associated with the acoustic emission event at point (15). The voltage output of the device (13) described herein is usually measured by means of an impedance matching amplifier (16) that drives the output cables (17). Such an amplifier (16) must have a high input impedance (>5 Megohms) with a very small equivalent input capacitance (<5 pF). Such a matching amplifier (16) either can be a separate item or it can be incorporated into the structure of the transducer. FIG. 3 also shows the elements of displacement calibration as generated by a step force function at position (18) on the surface (19) of the body (14). The displacement-time function, z=f(t), describes the displacement of the surface and is known. The calibration procedure is partly described in the ASTM Standard E 1106-86 and by Breckenridge.

In order for the tip of the active element (4) to be able to follow the motion of the surface of interest, it must be cemented with a rigid cement. Phenyl salicylate is a cement that has a special property. It provides a rigid bond for acoustic coupling but is weak enough to be sheared off easily without damaging the element tip (4) when the user wishes to remove the transducer (13) from the working surface (19).

Figure 4:
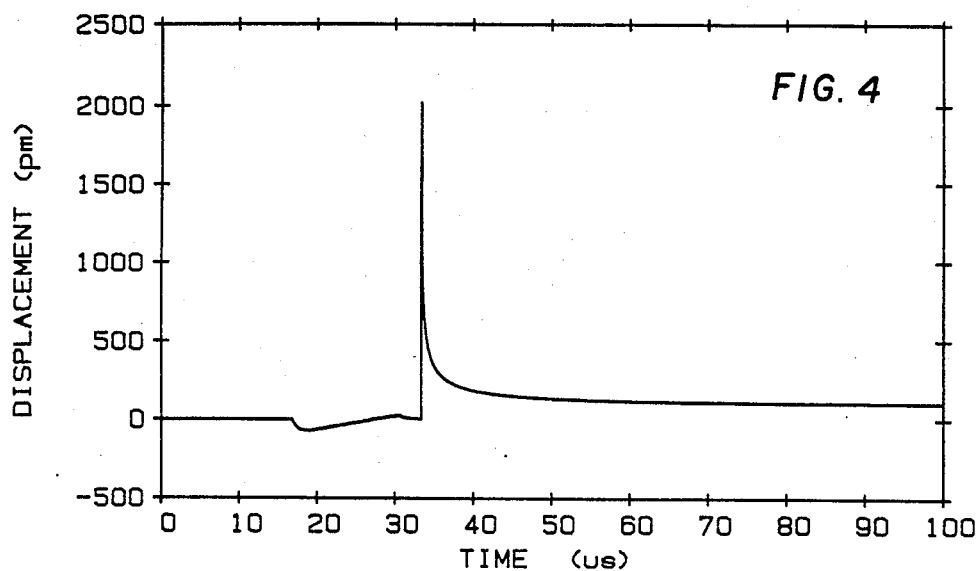
FIG. 4 is a graph of the theoretically expected tangential displacement as a function of time for a point on a half space of steel as caused by a point-force step function.
Figure 5:
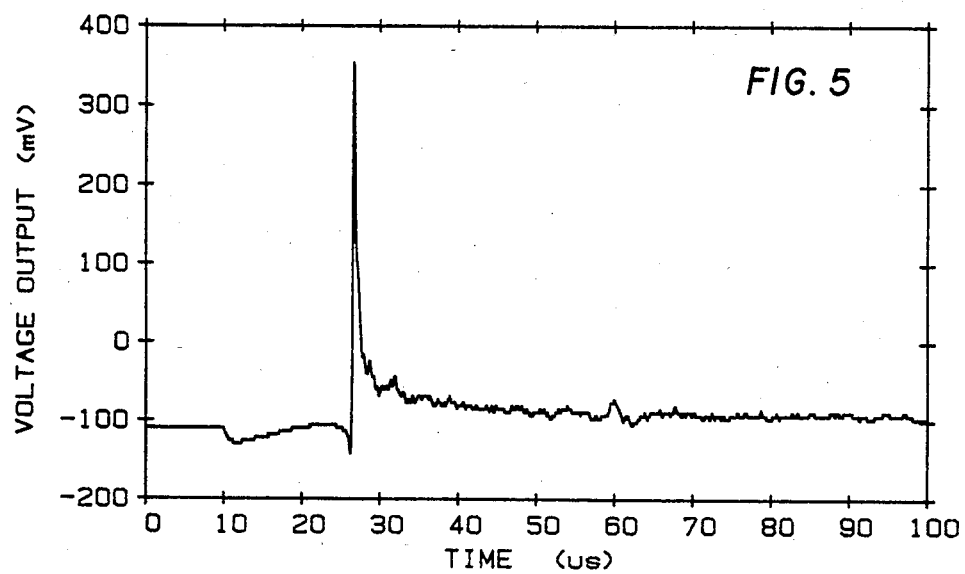
FIG. 5 is a graph of the voltage output of the acoustic emission transducer of this disclosure for tangential motion as a function of time.

Referring to FIG. 4, this figure shows a graph of the tangential component of displacement as calculated as a function of time from elastic theory. This theoretical result is calculated for a steel body under the assumptions of a semi-infinite half space which is excited at a remote point on its surface by a point step force function and represents the tangential displacement of a point on the surface. Pekeris and others have forecast this theoretical result for this physical situation. FIG. 5 shows the voltage output from the tangential displacement transducer as described in this invention as a function of time. The equivalent experimental condition to the theory of Pekeris is simulated by the use of a large steel cylinder that has dimensions of 0.9 m in diameter and 0.45 m in thickness. Both top and bottom surfaces are flat and parallel to each other. This steel cylinder acts like an infinite half space for the first 120 microseconds after an initiating calibration event. For times longer than that the first surface reflections begin to interfere. The experimental equivalent of the point step force function is the breaking of a glass capillary. The features of the steel block and the glass capillary source is described in the literature by Breckenridge.

Figure 6:
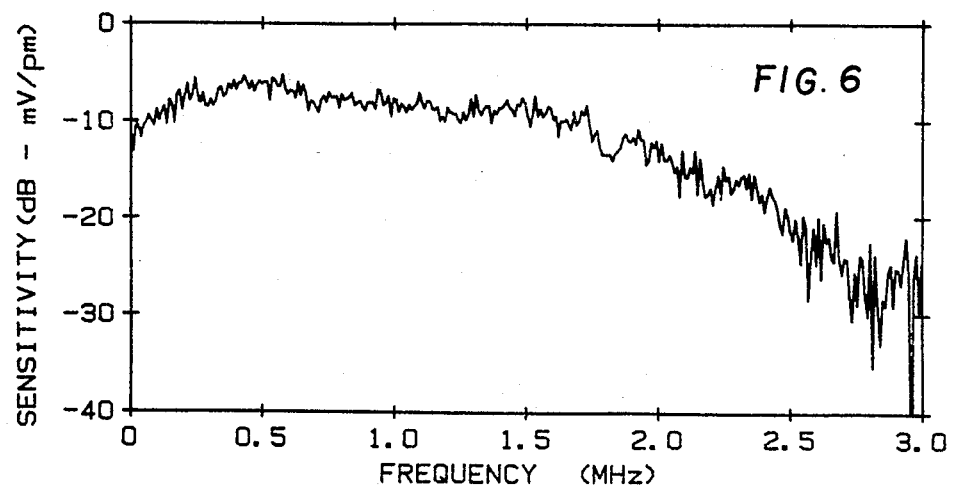
FIG. 6 is a graph showing the displacement response as a function of frequency in terms of volts output per unit displacement. This is obtained from the time voltage wave form of FIG. 5.

It is apparent from comparison of FIG. 4 and FIG. 5 that the tangential motion sensing transducer of this invention produces a voltage-time output that closely matches the calculated time function for the tangential component of the surface displacement. Using a mechanism that allows the stress on the glass capillary to be measured at the instant of fracture when the stress is released, it is possible to calibrate the voltage output against the expected displacement at the point of location of the transducer. Such a calibration is shown in FIG. 6. This is a comparison of the voltage output as in FIG. 5 to the expected tangential displacement as calculated from theory, the results of that being shown in FIG. 4. This comparison is a point by point division in frequency space of the frequency response obtained from FIG. 4 and 5. This provides the expected sensitivity, ie., voltage output from the described device per the surface displacement as a function of frequency.

As a result of the particular arrangement and attachments of this invention and testing thereof, the dynamic tangential surface displacement at a point on a mechanical body can be accurately measured. This invention provides a tool by which the dynamic displacement which is directly related to a specific physical quantity, of tangential displacement, can be directly inferred from the voltage output of the invention described herein. This represents a considerable improvement over those of the prior art.

While this apparatus herein disclosed forms a preferred embodiment of this invention, this invention is not limited to the specific apparatus described. Changes can be made therein without departing from the scope of the invention which is defined in the appended claims. For example, it will be understood that the selection of the material of the active element will be made dependent on the material of which the structure of interest is made and that the selection of the material for compound backing construction will be made dependent upon the material of which the active element is constructed. The scope of the invention will not be altered by the addition of minor facets, such as self contained impedance matching preamp, an electrical shielding case, and any thin material covering faces for the purpose of protecting the active element.

What is claimed is:

1. A transducer that acts as a point receiver and has a broad band frequency response for elastic waves that manifest themselves as surface waves which are characterized by motion parallel to the surface of a solid body, comprising:

(a) a piezoelectric element having two parallel plane faces of contact, one being a rear face for attachment to a backing member and the other being a front face for coupling to the solid body, the area of the rear face being much larger than the front face, and the cross section of the piezoelectric element continuously decreasing to the front face, the two faces comprising sensing electrodes;

(b) a backing member comprising a first part attached to the piezoelectric element and having an acoustic impedance nearly equal to the acoustic impedance of the piezoelectric element, and a second part having an acoustic impedance similar to the first part but having higher ultrasonic attenuation, and the first part being much larger than the piezoelectric element and having an irregularly shaped reflecting surface to provide a wide range of reflection paths possessing a wide range in delay times;

(c) a leveling means for insuring that the front face of contact of the piezoelectric element to the solid body of interest makes parallel plane contact with that surface; and (d) a means for coupling the transducer to the solid body of interest that will provide tight elastic and acoustic coupling between the small front face of the transducer element and the elastic medium of the solid body.

2. A transducer according to claim 1, wherein the ratio of the rear to front face areas of the piezoelectric element is larger than 250 to 1.

* * * * *